United States Patent [19]
Unsworth et al.

[11] Patent Number: 5,693,090
[45] Date of Patent: Dec. 2, 1997

[54] HEART VALVE PROSTHESIS

[75] Inventors: William David Unsworth, Warrington; Gianni Davide Angelini, Bristol, both of United Kingdom; Claudio Pistolesi, Monteriggioni, Italy

[73] Assignee: Cardio Carbon Company, Ltd., United Kingdom

[21] Appl. No.: 732,225

[22] PCT Filed: Apr. 18, 1995

[86] PCT No.: PCT/GB95/00887

§ 371 Date: Nov. 26, 1996

§ 102(e) Date: Nov. 26, 1996

[87] PCT Pub. No.: WO95/28898

PCT Pub. Date: Nov. 2, 1995

[30] Foreign Application Priority Data

Apr. 27, 1994 [GB] United Kingdom .................. 9408314

[51] Int. Cl.$^6$ ..................................................... A61F 2/24
[52] U.S. Cl. ................................................. 623/2; 137/527
[58] Field of Search ................................. 623/2; 137/521, 137/527

[56] References Cited

U.S. PATENT DOCUMENTS

| 3,938,197 | 2/1976 | Milo . |
| 5,061,278 | 10/1991 | Bicer ............................................. 623/2 |

FOREIGN PATENT DOCUMENTS

| 2 657 248 | 7/1991 | France . |
| 1222264 | 4/1986 | U.S.S.R. ..................................... 623/2 |
| 2241304 | 8/1991 | United Kingdom ....................... 623/2 |

Primary Examiner—Mary Beth Jones
Attorney, Agent, or Firm—Klima & Hopkins, P.C.

[57] ABSTRACT

The heart valve prosthesis comprises a substantially annular valve body having leaflets pivotally mounted to the valve body to be pivotable between respective open positions, in which blood is permitted to pass through the valve, and respective closed positions in which blood flow through the valve is substantially inhibited. The valve body is constructed of at least two part-annular elements and each respective leaflet is provided with at least two spaced pivot formations, each arranged to engage with a respective complementary pivot formation provided on a different part annular element. The annular body is assembled from the sub-elements and secured around the leaflets to provide a rigid annular body without the need for deformation or deflection of the annular body on assembly.

21 Claims, 2 Drawing Sheets

HEART VALVE PROSTHESIS

The present invention relates to a heart valve prosthesis, and in particular to a bileaflet heart valve prosthesis.

Bileaflet heart valve prostheses are known from, for example, European patent specification EP-A-289404 which discloses a bileaflet prosthetic heart valve having a pair of valve sealing leaflets pivotally mounted in an annular support body, the leaflets being pivotal to permit or restrict blood flow through the valve. To assemble the valve, the annular support body, which is unitary, is resiliently deformed to an extent to enable the pivot formations on the leaflets to be received in corresponding formations on the body, the annular body is then allowed to return to its original shape thereby returning the pivot formations of the leaflets in the formations on the annular body. Deflection of the resilient annular support body during assembly inherently subjects the annular support body to stresses; furthermore the requirements that the support ring be deformable to permit mounting of the leaflets during assembly runs contrary to the requirement that the ring must be rigid enough to ensure that muscular forces acting on the ring when in position in the heart must not cause sufficient deflection of the ring to enable the leaflets tb become detached therefrom.

An improved prosthetic heart valve has now been devised which alleviates the above-mentioned disadvantages with known prostheses.

According to a first aspect, the present invention provides a heart valve prosthesis comprising a substantially annular valve body having pivot formations arranged to engage with complementary pivot formations provided on each of a respective pair of leaflets such that the leaflets are pivotally mounted to the valve body to be pivotable between respective open positions, in which blood is permitted to pass through the valve, and respective closed positions in which blood flow through the valve is substantially inhibited, wherein the valve body is constructed of at least two part-annular elements and each respective leaflet is provided with at least two spaced pivot formations, each arranged to engage with a respective complementary pivot formation provided on a different part-annular element.

The annular valve body is preferably substantially circular or ring like in projection. Alternatively, the annular valve body may be substantially square, or oblong in projection, and the term substantially annular should be interpreted to cover such constructions.

It is preferred that the annular body is of two part construction comprising a pair of semi-annular part-annular elements connected to one another at diametrically opposed positions.

In this embodiment it is preferred that each semi-annular element of the valve body carries pivot formations arranged to complementarily engage with respective pivot formations provided on each of the leaflets. Desirably, in the closed position, the leaflets define a diametrical sealing line which is arranged to extend transversely (preferably substantially perpendicularly) to a line joining the diametrically opposed connection positions of the semi-annular valve body elements.

It is preferred that the annular valve body is substantially rigid when constructed, advantageously comprised of biocompatible metallic construction preferably comprising titanium or a titanium alloy.

It is preferred that mechanical fixing means such as for example connecting pins are used to secure the part-annular elements of the valve body. In addition, or alternatively, the respective part-annular elements may be chemically bonded by adhesives, or more preferably by means of fusion bonding or welding at the respective connection positions.

It is particularly preferred that each of the annular valve body and the leaflets are provided with a coating layer of a material having good biocompatibility properties, preferably being a haemocompatible material.

Such a material may for example be pyrolytic carbon or, more preferably, the form of carbon commonly known as "diamond like" carbon. An alternative biocompatible material comprises titanium nitride. When a biocompatible coating is applied to the biocompatible metal (which, as previously indicated, is preferably of titanium or a titanium alloy), it is preferred to apply successive layers by chemical vapour deposition (generally plasma assisted chemical vapour deposition). It is preferred that the nitride (that is, $Ti_xN_y$), is initially applied. When a carbon coating is required, the nitride is preferably followed by a mixed carbide/nitride (that is, $Ti_xN_yC_z$), and then by the carbide (that is $Ti_xC_z$), followed by carbon itself. The latter is preferably in the form of diamond-like carbon.

It is preferred that the hinge lines about which the respective leaflets pivot are substantially parallel both to one another and also preferably the diametrical sealing line. Desirably, the pivot formations of the leaflets extend away from a respective pivot point on a respective hinge line at an inclined angle relative thereto such that the hinge formations of a respective leaflet splay away from one another at the hinge line.

Desirably, the pivot formations of the annular valve body comprise respective shaped recessed pivot seats provided on the internal wall of the annular body. Advantageously the recessed seats are substantially triangular in shape.

In a preferred embodiment, the pivot formations of the annular valve body are provided with communication recesses or channels to permit some blood flow from upstream to downstream through the valve via the pivot formations. This enables lubrication of the pivot formations of the leaflets in the pivot formations of the annular body to be achieved, and results in improved performance. It is believed that the provision of pivot formations on the valve body having communicating recesses or channels defining a blood flow path from upstream to downstream is novel and inventive per se.

Desirably, the communicating recesses or channels extend in opposed directions axially of the valve. Advantageously, the recesses or channels are formed integrally with the pivot formations of the valve body, preferably tapering toward the pivot formation to improve blood flow characteristics.

It is preferred that the annular body is provided with stop formations projecting inwardly of the annular body. The stop formations are provided to contact portions of the leaflets when the leaflets are in their closed position. Desirably the stop formations are provided on diametrically opposed portions of the annular body, preferably being intersected by the diametrical sealing line. Advantageously, the stop formations have a surface profile which is streamlined to taper or narrow in the upstream direction of the valve.

According to a further aspect, the invention provides a method of manufacturing a prosthetic heart valve which method comprises assembling a plurality of sub-elements to form an annular valve body around a pair of leaflets such that pivot formations provided on respective leaflets engage with corresponding complementary pivot formations provided on different ones of said sub-elements and subsequently securing said sub-elements relative to one another to form an effectively unitary valve body around the leaflets.

It is preferred that the sub-elements are bonded together thereby to be secured relative to one another.

Desirably, the entire prosthesis, and at least the annular valve body and leaflets are coated with a biocompatible material.

The invention will now be further described in a specific embodiment by way of example only and with reference to the accompanying drawings, in which.

Figure 1:
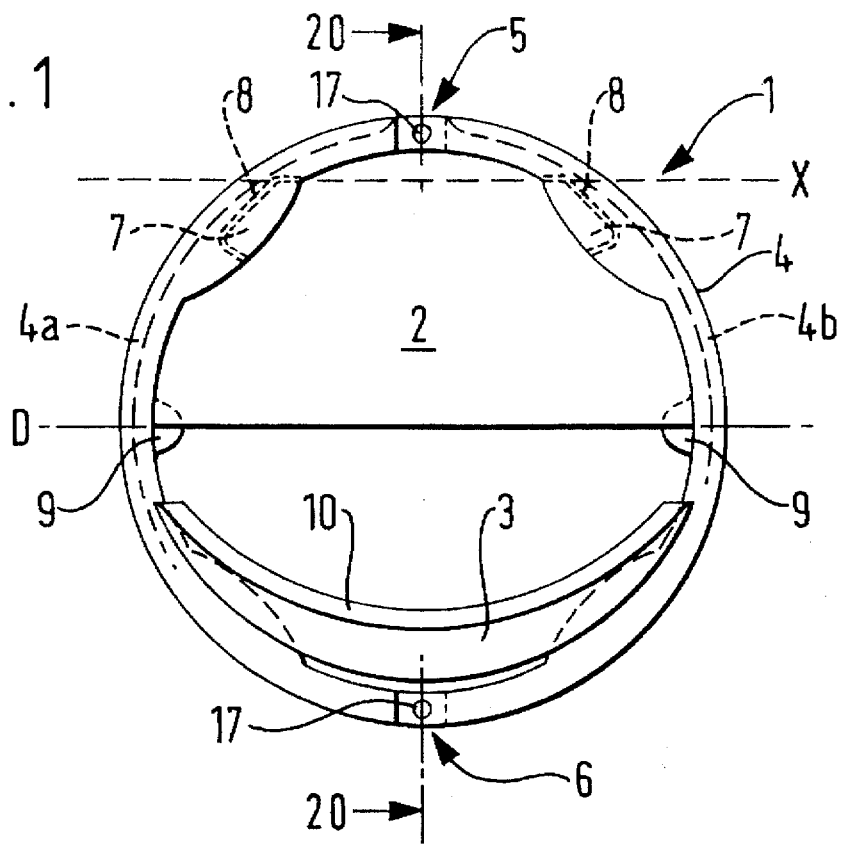
FIG. 1 is a schematic plan elevation of an exemplary heart valve prosthesis according to the invention.
Figure 2:
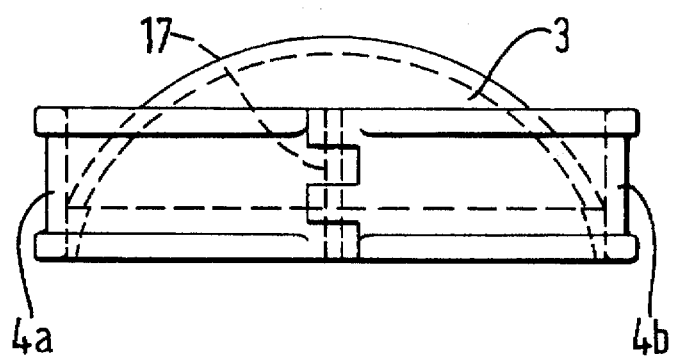
FIG. 2 is an end elevation showing a semi-annular element comprising the annular valve body of the heart valve prosthesis of FIG. 1.
Figure 3:
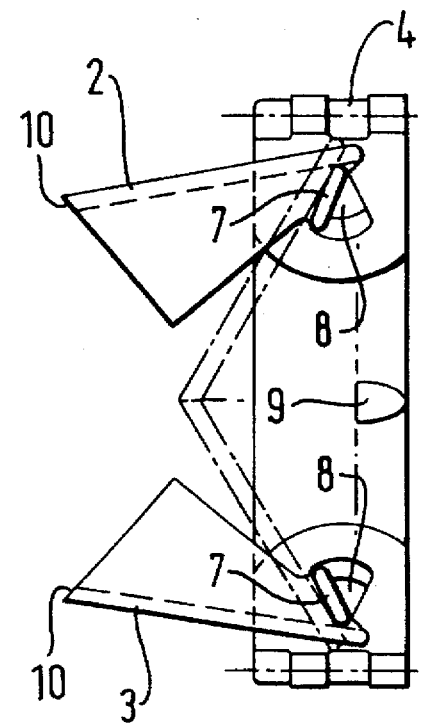
FIG. 3 is a schematic sectional view of the heart valve prosthesis of FIG. 1 along the axis 20—20.
Figure 4A:
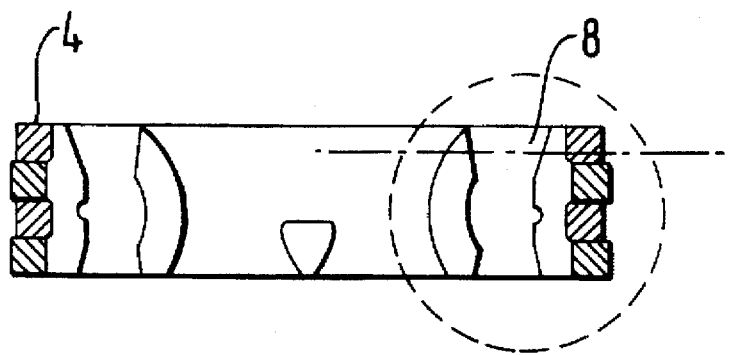
FIG. 4a is a schematic sectional view (not showing the leaflets), similar to the view of FIG. 3, of an alternative embodiment of heart valve prosthesis according to the invention.
Figure 4B:
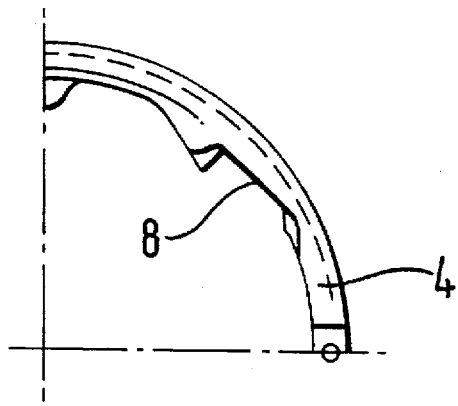
FIGS. 4b and 4c are detail plan views of a part of the prosthesis of FIG. 4a showing improved pivot formations.
Figure 4C:
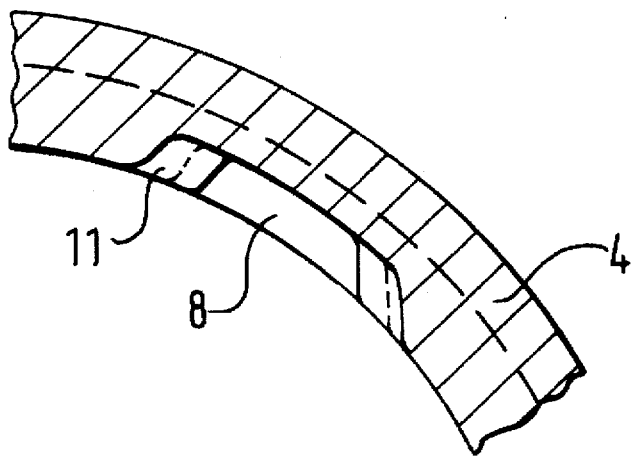
Figure 4D:
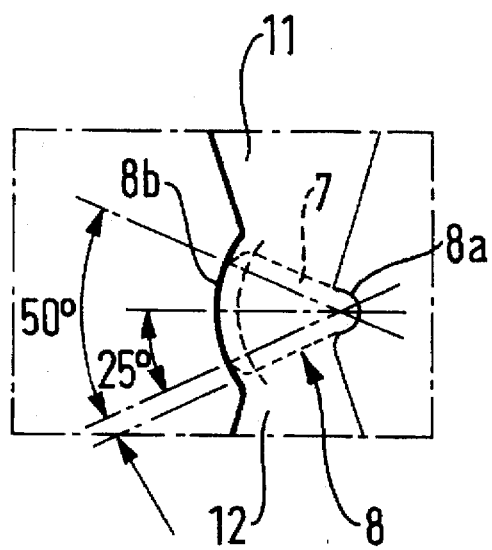
FIG. 4d is a detail side view of a pivot formation of the valve body shown in FIGS. 4a to 4c.

Referring to the drawings, there is shown a bileaflet prosthetic heart valve 1 comprising a pair of leaflets 2,3 pivotally mounted in an annular valve body 4. As shown in FIG. 1, for explanation purposes leaflet 2 is in its closed position whereas leaflet 3 is in its open position. In use, both leaflets would either simultaneously be in their open positions, closed positions or corresponding intermediate positions, as the valve opens and closes with the pulsing of blood through the heart. FIG. 3 shows the valve with leaflets 2,3 in their open positions (in bold lines) and in their closed positions (in dashed lines). FIG. 2 shows the leaflets 2,3 in their closed positions.

The annular valve body 4 is constructed of two identical semi-annular sub-elements 4a,4b which are joined at diametrically opposed positions 5,6 optionally by means of respective connecting pins 17 passing through aligned bores in overlapping portions of each element 4a,4b. The sub-elements 4a,4b are formed of titanium, such that when assembled into a complete annulus 4 respective portions of the sub-elements 4a,4b at the positions 5,6 may be bonded to one another by means of a fusion welding process for example.

Respective pairs of pivot formations 7 are provided projecting from each leaflet 2,3 (only those on leaflet 2 are shown in FIG. 1) the pivot formations 7 extending outwardly relative to one another from a hinge line X and being received in respective triangular shaped recessed pivot seats 8 provided in the annular body 4. It is important to note that the pivot seats 8 for receiving the pivot formations 7 of a particular leaflet (e.g. leaflet 2) are positioned one on each separate sub-element 4a,4b. In this way, the annular body 4 may be assembled and secured around the leaflets 2,3 and subsequently secured to provide a rigid annular body without the need for deformation or deflection of the annular body as is necessary for prior art constructions.

Stop formations 9 are provided on diametrically opposed portions of sub-elements 4a,4b, being intersected by the diametrical sealing line D formed along the sealing edges 10 of the leaflets 2,3 when oriented in their closed position. As shown most clearly in FIG. 3, the stop formations are streamlined such that they taper in the upstream direction of the valve for reasons of haemodynamic efficiency.

It is preferred that the leaflets 2,3 and the valve body 4 are coated in a coating having good haemodynamic properties such as for example diamond-like carbon. Processes for coating prosthetic bodies in diamond-like carbon are known from, for example, U.K. patent specification GB-A-2114963 and European patent specification EP-A-302717.

Referring to FIGS. 4a to 4d, there is shown part of a heart valve prosthesis which is generally similar to that shown in FIGS. 1 to 3, but having improved pivot seats 8 for co-operation with the pivot formations 7 on the respective leaflets (not shown). In this embodiment, the pivot seats 8 comprise an apex portion 8a and opposite recessed portion 8b arranged to hold the pivot formations of the leaflet captive whilst the respective leaflet pivots between open and closed positions. Communicating with the pivot seat 8, and extending in the axial direction of the valve, are respective recess or channel portions 11,12 provided in the surface of the valve body 4, which permit blood to flow through the pivot seats 8 during operation of the valve. This arrangement is advantageous since it enables the pivot seats to be continually "washed" with blood and prevent accumulation and coagulation of blood in the pivot seats. The recess or channel portions 11,12 taper towards the pivot seat 8 to improve the blood flow to and from the pivot seat.

What is claimed:

1. A heart valve prosthesis comprising a substantially annular valve body having pivot formations arranged to engage with complementary pivot formations provided on each of a respective pair of leaflets such that the leaflets are pivotally mounted to the valve body to be pivotable between respective open positions, in which blood is permitted to pass through the valve, and respective closed positions in which blood flow through the valve is substantially inhibited, wherein the valve body is constructed of at least two part-annular elements and each respective leaflet is provided with at least two spaced pivot formations, each arranged to engage with a respective complementary pivot formation provided on a different part of the at least two part-annular elements.

2. A heart valve prosthesis according to claim 1, wherein the annular body is of two part construction comprising a pair of semi-annular elements connected to one another at diametrically opposed positions.

3. A heart valve prosthesis according to claim 2, wherein in the closed position, the leaflets define a diametrical sealing line which is arranged to extend transversely to a line joining the diametrically opposed connection positions of the semi-annular valve body elements.

4. A heart valve prosthesis according to claim 1, wherein the part-annular elements of the valve body are secured together by mechanical fixing means.

5. A heart valve prosthesis according to claim 1, wherein the respective part-annular elements are bonded together.

6. A heart valve prosthesis according to claim 1, which is of rigid metallic construction.

7. A heart valve prosthesis according to claim 6 comprising titanium or a titanium alloy.

8. A heart valve prosthesis according to claim 1, which has thereon a coating layer of a biocompatible material.

9. A heart valve prosthesis according to claim 1, wherein the respective leaflets pivot about respective hinge lines, the pivot formations of the leaflets extending away from a respective pivot point on a respective hinge line at an inclined angle relative thereto such that the hinge formations of a respective leaflet splay away from one another at the hinge line.

10. A heart valve prosthesis according to claim 1, wherein the pivot formations of the annular valve body comprise respective shaped recessed pivot seats provided on the internal wall of the annular body.

11. A heart valve prosthesis according to claim 1, wherein the pivot formations of the annular valve body are provided with communication recesses or channels to permit some blood flow from upstream to downstream through the valve via the pivot formations.

12. A heart valve prosthesis according to claim 11, wherein the recesses or channels are formed integrally with the pivot formations of the valve body, tapering toward the pivot formation to improve blood flow characteristics.

13. A heart valve prosthesis according to claim 1, wherein the annular body is provided with stop formations projecting inwardly of the annular body and the stop formations are arranged to contact portions of the leaflets when the leaflets are in their closed position.

14. A heart valve prosthesis according to claim 13, wherein the stop formations have a surface profile which is streamlined to taper or narrow in the upstream direction of the valve.

15. A method of manufacturing a prosthetic heart valve which method comprises assembling a plurality of sub-elements to form an annular valve body around a pair of leaflets such that pivot formations provided on respective leaflets engage with corresponding complementary pivot formations provided on different ones of said sub-elements and subsequently securing said sub-elements relative to one another to form an effectively unitary valve body around the leaflets.

16. A method according to claim 15, wherein the sub-elements are secured relative to one another by mechanical fixing means.

17. A method according to claim 15, wherein the sub-elements are secured relative to one another by means of bonding.

18. A method according to claim 15, wherein a biocompatible coating is applied to components comprising the heart valve.

19. A method according to claim 18, wherein the biocompatible coating is applied as successive layers of varying composition.

20. A method according to claim 18, wherein the biocompatible coating is applied by chemical vapour deposition.

21. A method according to claim 18, wherein the biocompatible coating comprises an outermost layer of carbon.

* * * * *